(12) United States Patent
Motzer et al.

(10) Patent No.: US 8,983,794 B1
(45) Date of Patent: Mar. 17, 2015

(54) METHODS AND SYSTEMS FOR NON-DESTRUCTIVE COMPOSITE EVALUATION AND REPAIR VERIFICATION

(75) Inventors: William P. Motzer, Seattle, WA (US);
Gary E. Georgeson, Tacoma, WA (US);
Scott W. Lea, Renton, WA (US); James J. Troy, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 1131 days.

(21) Appl. No.: 12/897,428

(22) Filed: Oct. 4, 2010

(51) Int. Cl.
*G01C 9/00* (2006.01)

(52) U.S. Cl.
USPC .............. 702/150; 702/33; 702/34; 702/35; 702/36; 702/39; 702/151; 702/152; 702/153; 702/155; 702/159

(58) Field of Classification Search
USPC ........... 702/150, 33, 34, 35, 36, 39, 151, 152, 702/153, 155, 159
See application file for complete search history.

(56) References Cited

U.S. PATENT DOCUMENTS

| | | | |
|---|---|---|---|
| 6,033,415 A * | 3/2000 | Mittelstadt et al. | 606/130 |
| 2003/0048459 A1 * | 3/2003 | Gooch | 356/620 |
| 2004/0254677 A1 * | 12/2004 | Brogardh et al. | 700/245 |
| 2008/0141778 A1 * | 6/2008 | Bosselmann et al. | 73/633 |
| 2009/0086014 A1 | 4/2009 | Lea et al. | |
| 2009/0086199 A1 | 4/2009 | Troy et al. | |
| 2010/0228506 A1 * | 9/2010 | Motzer et al. | 702/56 |

OTHER PUBLICATIONS

U.S. Appl. No. 12/631,810, filed Dec. 5, 2009.

* cited by examiner

*Primary Examiner* — Hyun Park
(74) *Attorney, Agent, or Firm* — Armstrong Teasdale LLP

(57) ABSTRACT

A non-destructive inspection system for a structure is described. The inspection system includes a local positioning system (LPS) configured for determining position and orientation of objects relative to a structure coordinate system, a six degree-of-freedom digitizer operable for at least one of temporary attachment to the structure and placement proximate the structure, a non-destructive sensor array, and a processing device.

19 Claims, 9 Drawing Sheets

METHODS AND SYSTEMS FOR NON-DESTRUCTIVE COMPOSITE EVALUATION AND REPAIR VERIFICATION

BACKGROUND

The field of the disclosure relates generally to composite repair verification, and more specifically, to methods and systems for non-destructive composite evaluation and repair verification.

With the increased usage of composites for aircraft structures, obtaining rapid, low-cost, yet high resolution non-destructive evaluation (NDE) data on in-service composite aircraft has become more important, and yet still remains a need within the aerospace industry. While damage assessment may be done with a lower resolution scanner or handheld single transducer system, composite repair verification requires high spatial resolution to quantify porosity. Currently only scanned pulse echo ultrasound is capable of providing the zoned porosity measurements required for validating composite scarfed and bonded repairs. Currently validation of such repairs can only be performed using expensive equipment.

One existing validation tool includes a handheld ultrasonic transducer (UT) system with individual transducers or phased array systems. However, handheld scanning is very slow and cannot produce the images required in many cases, for example, the measurement of porosity that is utilized in composite repairs. Moreover, such phased array UT systems are very expensive and somewhat complex.

Another validation tool is a mobile automated scanner (MAUS) which is a system that attaches to the structure being validated, such an aircraft, and scans individual UT probes or arrays. The MAUS scanner is also expensive, complicated to operate (using it requires specialized skills), and further requires two people to attach and run. As such, few potential users can afford it, and it is limited to minimally contoured structures because of the design of the flexible track and scanner arm, for example, it cannot do leading edges, or corners of structures having a radius.

A rapid scan tool is a variant of the phased array ultrasonic process, and uses a wheel probe, containing an array transducer, which is passed across the surface of a component generating a picture of the structure under test. While the rapid scan tool collects image data quickly, the cost and complexity of the system limit broad usage. Further, it is not designed for highly contoured surfaces, and has no three-dimensional imaging capability.

Other validation tools include a positional encoder capability to create scanned images and incorporate a manually manipulated radius-angle scanner arm. The scanner base incorporates encoders that register the position and orientation of the probe head. Systems with positional encoders are slow, and do not have the spatial resolution required for composite repair validation and porosity measurement. Further, they do not include a three-dimensional imaging capability.

The freehand area scanning tool (FAST) utilizes recent advances in the precision of IMU (Inertial Measurement Unit) devices and arrays to permit free-hand scanning for rapid NDE data collection. The FAST applies to many inspection applications, but the IMUs it is based upon do not currently have the spatial resolution for zoned porosity measurements in composite repairs.

BRIEF DESCRIPTION

In one aspect, a non-destructive inspection system for a structure is provided. The inspection system includes a local positioning system (LPS) configured for determining position and orientation of objects relative to the coordinate system of the structure, a six degree-of-freedom digitizer operable for at least one of temporary attachment to the structure and placement proximate the structure, a non-destructive sensor array, and a processing device. The digitizer includes a base and an articulated arm extending from the base and having a distal end. The local positioning system is configured for determining a position and orientation of the base of the digitizer in the coordinate system of the structure. The digitizer is further configured to determine a position of the distal end with respect to the base. The non-destructive sensor array is configured for attachment to the distal end of the articulated arm for movement across a surface of the structure in multiple positions and orientations. The processing device is configured to determine position and orientation data for the non-destructive sensor array based on the position and orientation of the digitizer base as determined by the LPS, and the position and orientation of the distal end of the digitizer as provided by the digitizer. The processing device is further configured to operate the sensor array for collection of scan samples relating to the structure, and to correlate the individual scan samples with the corresponding position and orientation data relating to the distal end of the digitizer to create an integrated representation of the scan volume of the structure, defined in the coordinate system of the structure.

In another aspect, a method for validating the integrity of a composite structure is provided. The method includes locating a six degree-of-freedom digitizer proximate the surface of the structure proximate an area to be validated, determining a position and an orientation of a reference portion of the digitizer in the coordinate system of the structure, configuring a distal end of an articulating arm of the six degree-of-freedom digitizer with a non-destructive evaluation sensor array, moving the non-destructive evaluation sensor array across the surface of the structure to be validated, tracking a position and orientation for the non-destructive evaluation sensor array based on the determined position and orientation of the reference portion of the digitizer and the position and orientation of the distal end of the digitizer with respect to the determined position and orientation of the reference portion of the digitizer, correlating data from the non-destructive evaluation sensor array with the position and orientation data from the distal end of the digitizer, and generating an integrated representation of the scan volume of the structure, defined in the coordinate system of the structure.

In still another aspect, a non-destructive inspection system for a structure is provided. The system includes a six-degree-of-freedom digitizer having a base and an articulated arm extending from the base and having a distal end, the digitizer configured to determine a position and orientation of the distal end with respect to the base, a local positioning system operable for determining a position and orientation of the digitizer base in the coordinate system of the structure, a non-destructive sensor array attached to the distal end of the digitizer, and a processing device. The processing device is configured to operate the sensor array for collection of scan samples relating to the structure from the sensor array as the sensor array is moved across the structure. The processing device is further configured to correlate the individual scan samples from the sensor array with corresponding position and orientation data relating to the sensor array from the digitizer and the position and orientation of the digitizer base from the local positioning system.

The features, functions, and advantages that have been discussed can be achieved independently in various embodiments or may be combined in yet other embodiments further details of which can be seen with reference to the following description and drawings.

DETAILED DESCRIPTION

The described embodiments are directed to methods and systems that combine three-dimensional metrology, non-destructive evaluation (NDE) array sensor technology, a local positioning system (LPS) and a rapid attachment capability to produce a low cost, high resolution, portable, three-dimensional NDE scanning process for verification of composite repairs and validation of other structures.

The embodiments enable more efficient aircraft composite repair by making validation of the repair simpler and more cost-effective than is presently possible. In embodiments, and as described in further detail below, attachment of an articulated measurement device to the composite material to be validated, allows free-form, high resolution scanning and imaging of interior damage/defects in composites. Validation of repairs and verification of other structures is therefore provided, even for structures with highly complex shapes. As further described herein, the system uses a local positioning system (LPS) to determine the position and orientation of a portion of the articulated device, such as a base of the articulated device, in the local coordinates of the structure being verified. With the position and orientation of the base of the articulated device known, a position and an orientation of any of the segments of the articulating arm of the device (including the distal end where the NDE sensor may be located) can be calculated in the local coordinates of the structure by using device kinematic variables, such as the device joint angles and segment lengths. As used herein, a coordinate system is the frame of reference defined by three orthogonal directions (X, Y, Z). Coordinate systems can be associated with both moving and stationary objects. Cartesian coordinates refer to a rectangular (orthogonal) coordinate system. Local coordinates refer to a coordinate system defined for a specific object.

Figure 1:
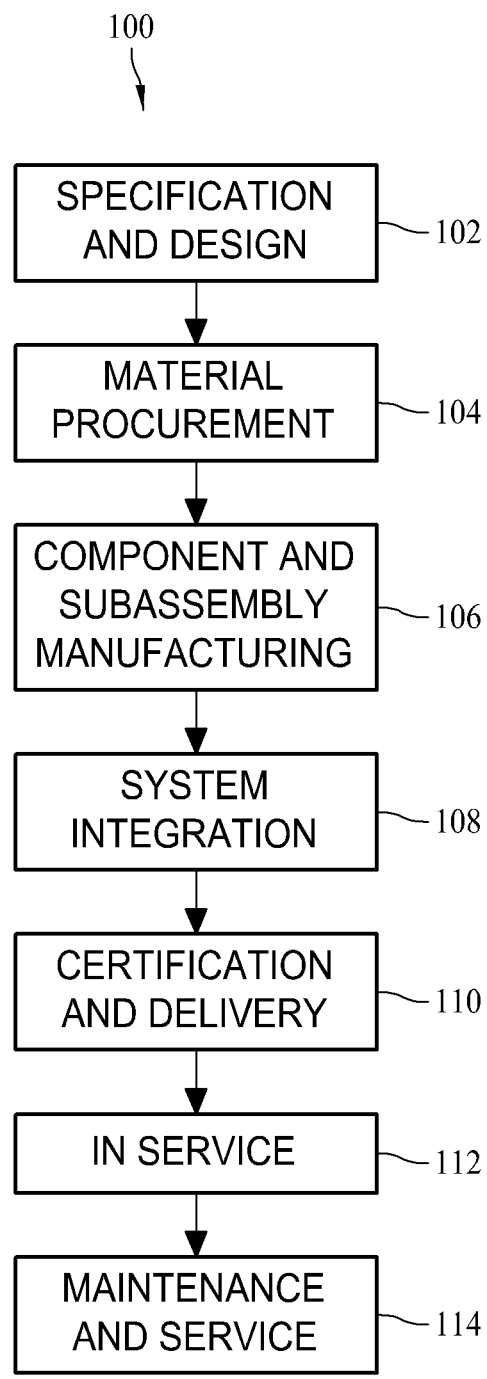
FIG. 1 is a flow diagram of an aircraft production and service methodology.
Figure 2:
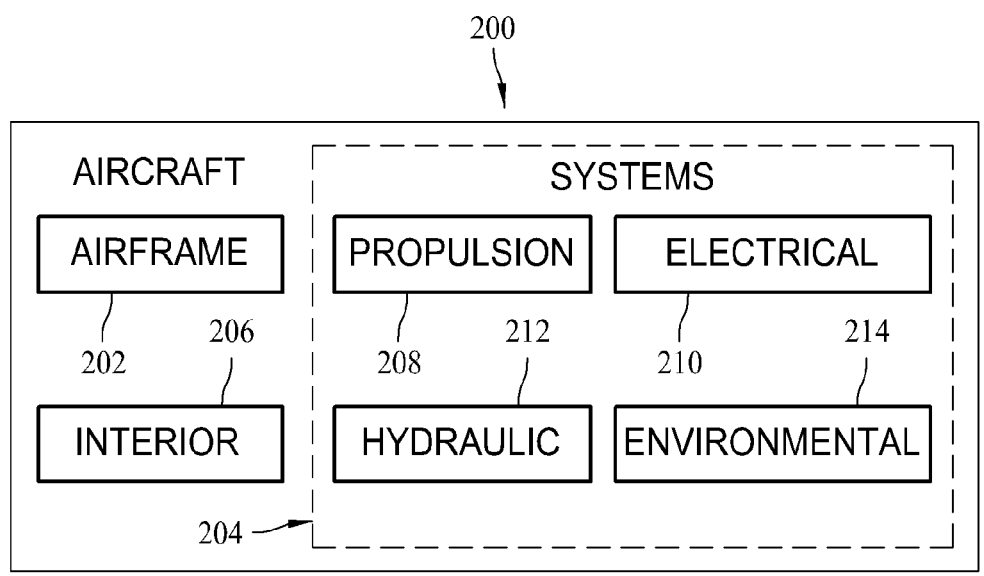
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
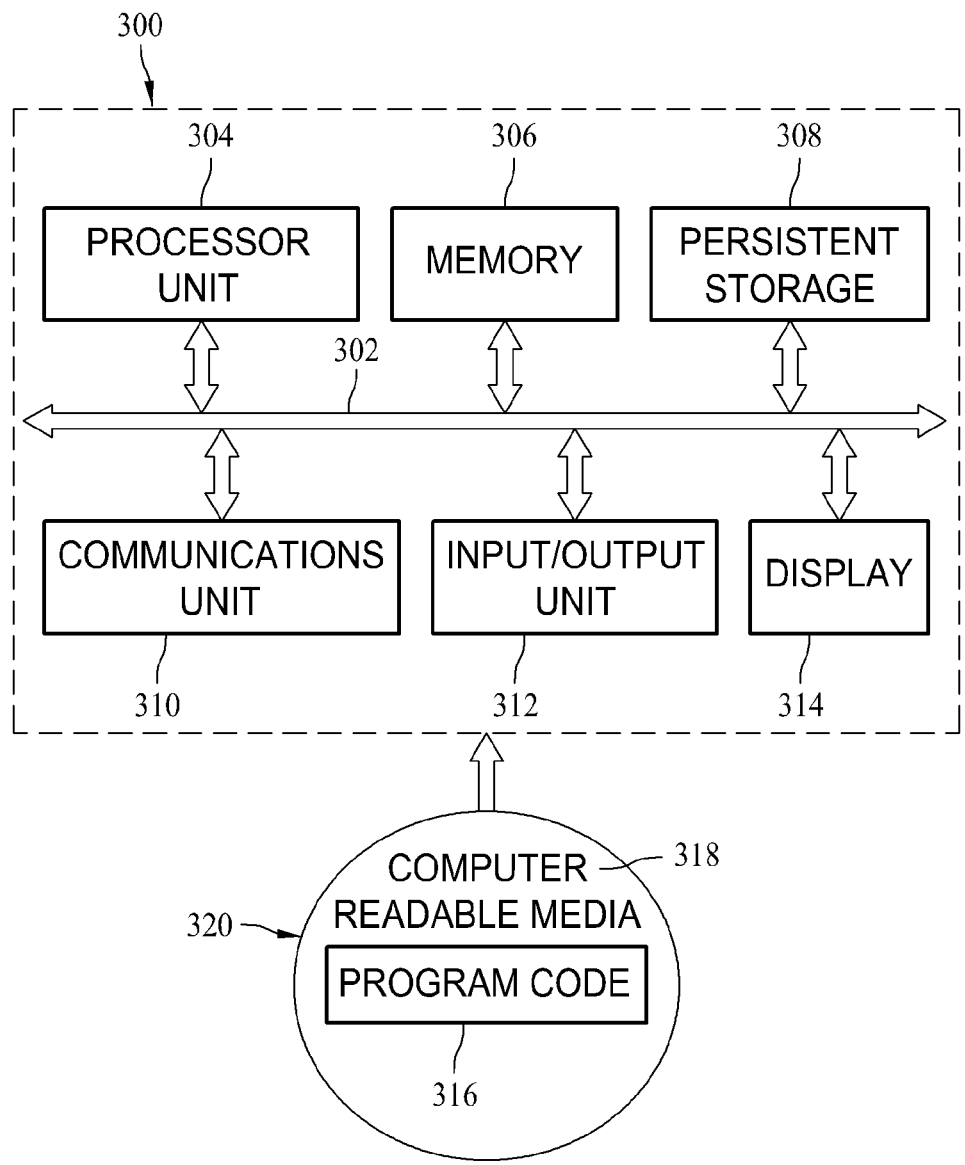
FIG. 3 is a diagram of a data processing system.

Turning now to FIG. 3, a diagram of a data processing system is depicted in accordance with an illustrative embodiment. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, without limitation, a random access memory or any other suitable volatile or non-volatile storage device. Persistent storage 308 may take various forms depending on the particular implementation. For example, without limitation, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, without limitation, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communication links.

Input/output unit 312 allows for input and output of data with other devices that may be connected to data processing system 300. For example, without limitation, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306. These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples. In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308. In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code or data.

In some illustrative embodiments, program code 316 may be downloaded over a network to persistent storage 308 from another device or data processing system for use within data processing system 300. For instance, program code stored in a computer readable storage medium in a server data processing system may be downloaded over a network from the server to data processing system 300. The data processing system providing program code 316 may be a server computer, a client computer, or some other device capable of storing and transmitting program code 316.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

As one example, a storage device in data processing system 300 is any hardware apparatus that may store data. Memory 306, persistent storage 308 and computer readable media 318 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, without limitation, memory 306 or a cache such as that found in an interface and memory controller hub that may be present in communications fabric 302.

Figure 4:
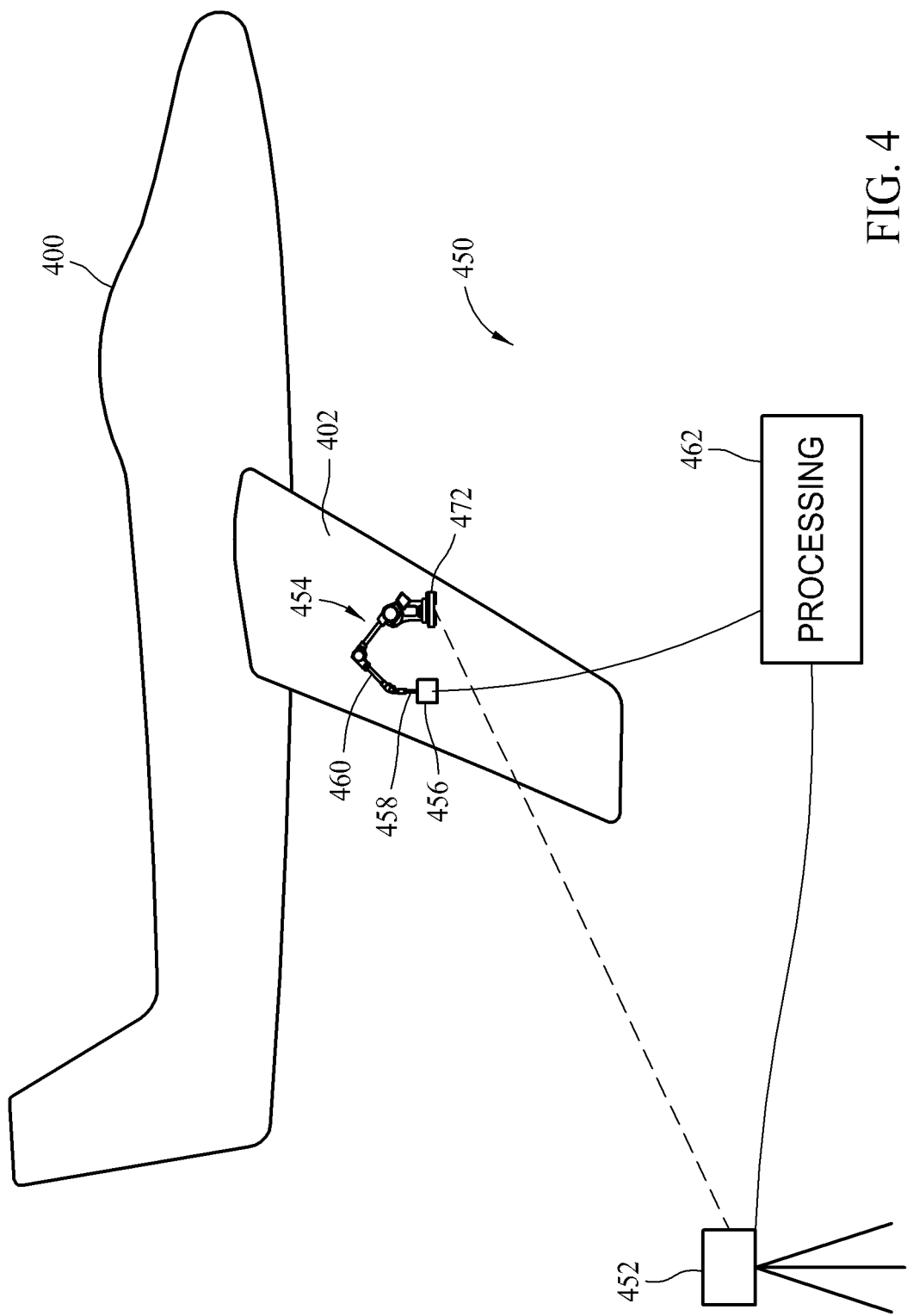
FIG. 4 is a depiction of an aircraft during validation of composite repairs to a wing.

FIG. 4 is a depiction of an aircraft 400 where composite repairs to a wing 402 are being validated. The inspection system 450 includes a local positioning system (LPS) 452, an articulated arm, six-degrees of freedom (DOF) digitizer 454, and a processing device 462. Digitizer 454 includes a sensor 456 mounted at the distal end 458 of the arm 460. Processing device 462 is capable of communications with digitizer 454, sensor 456, and in some embodiments, with LPS 452.

Figure 5:
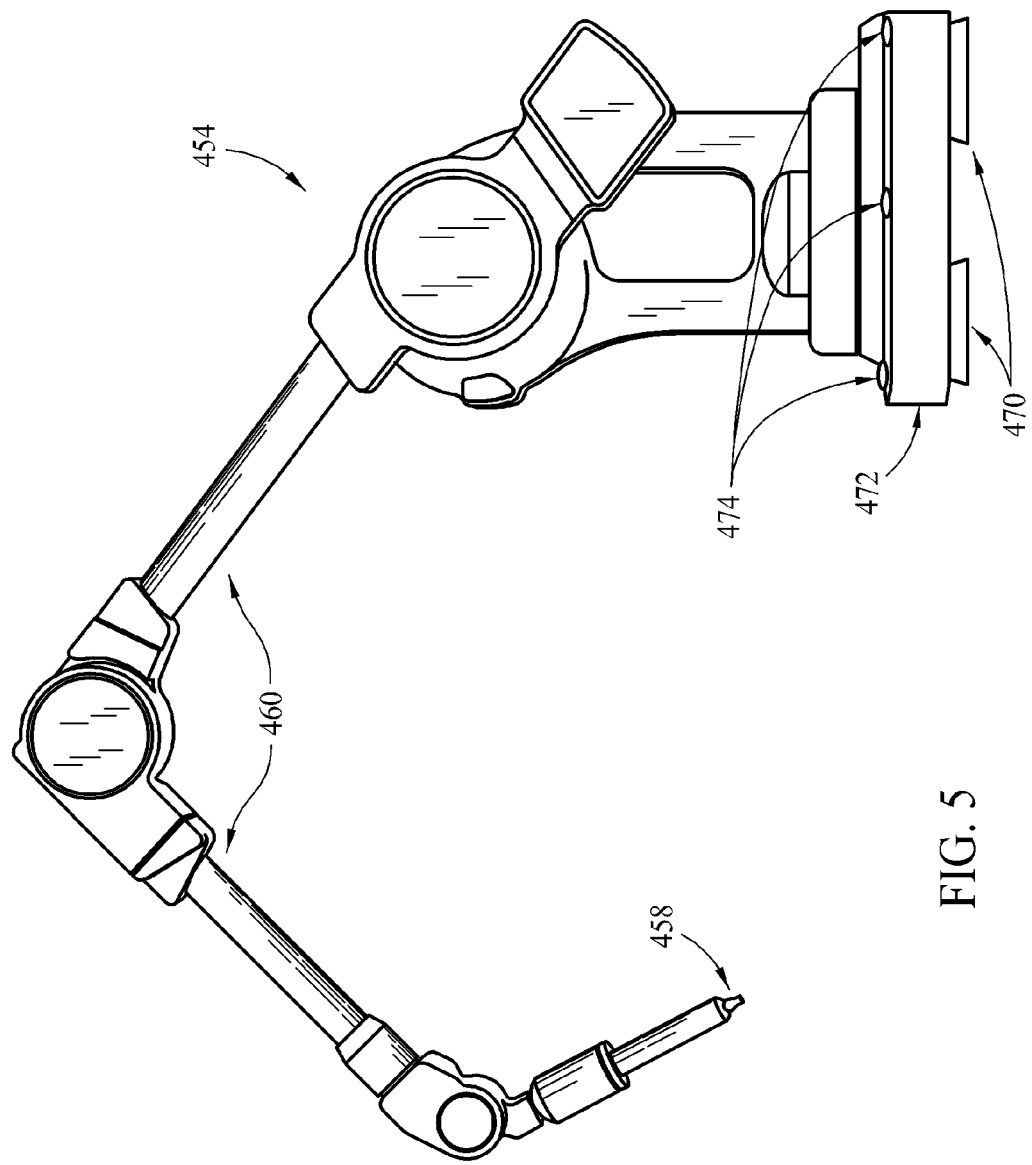
FIG. 5 is an illustration of an articulated arm six-degree-of-freedom (DOF) digitizer.

In some embodiments, the inspection system 450 is capable of performing a composite material inspection process that provides low cost, portable, high resolution, high speed, and multiple dimension NDE scanning for validating composite repairs and making damage assessments. The inspection system 450 takes advantage of advancements in six-DOF digitizers such as the articulated arm, six-DOF digitizer 454, which is shown in further detail in FIG. 5. One example of such a digitizer is the six degree-of-freedom version of the MicroScribe® desktop digitizer by Revware, Inc. Digitizer 454, has the ability to position and orient the last segment of its arm 460 (including the distal end 458) in space in at least some portion of its workspace. For clarity, digitizer 454 is shown in FIG. 5 without sensor 456 mounted at the distal end 458 of arm 460.

Due to the attachment of sensor array 456 to the distal end 458 of the articulated arm 460, sensor array 456 is sometimes referred to as having six dimensional movement across a surface of a structure, which means three dimensional movement for defining a position of the sensor array 456 and a three dimensional definition for orientation of the sensor array 456.

As further described, one embodiment of sensor array 456 utilizes scanned pulse echo ultrasonic inspection. The return signal amplitude and time-of-flight information produced by the sensor array 456 are collected at individual locations from the surface of the structure at a selected distance apart. The scanned data is combined into two-dimensional slices that represent return amplitude or time-of-flight images. When combined with the position and orientation data from the digitizer, the two-dimensional slices can be mapped to the surface contour and three-dimensional datasets of the scanned region can be produced.

Figure 8A:
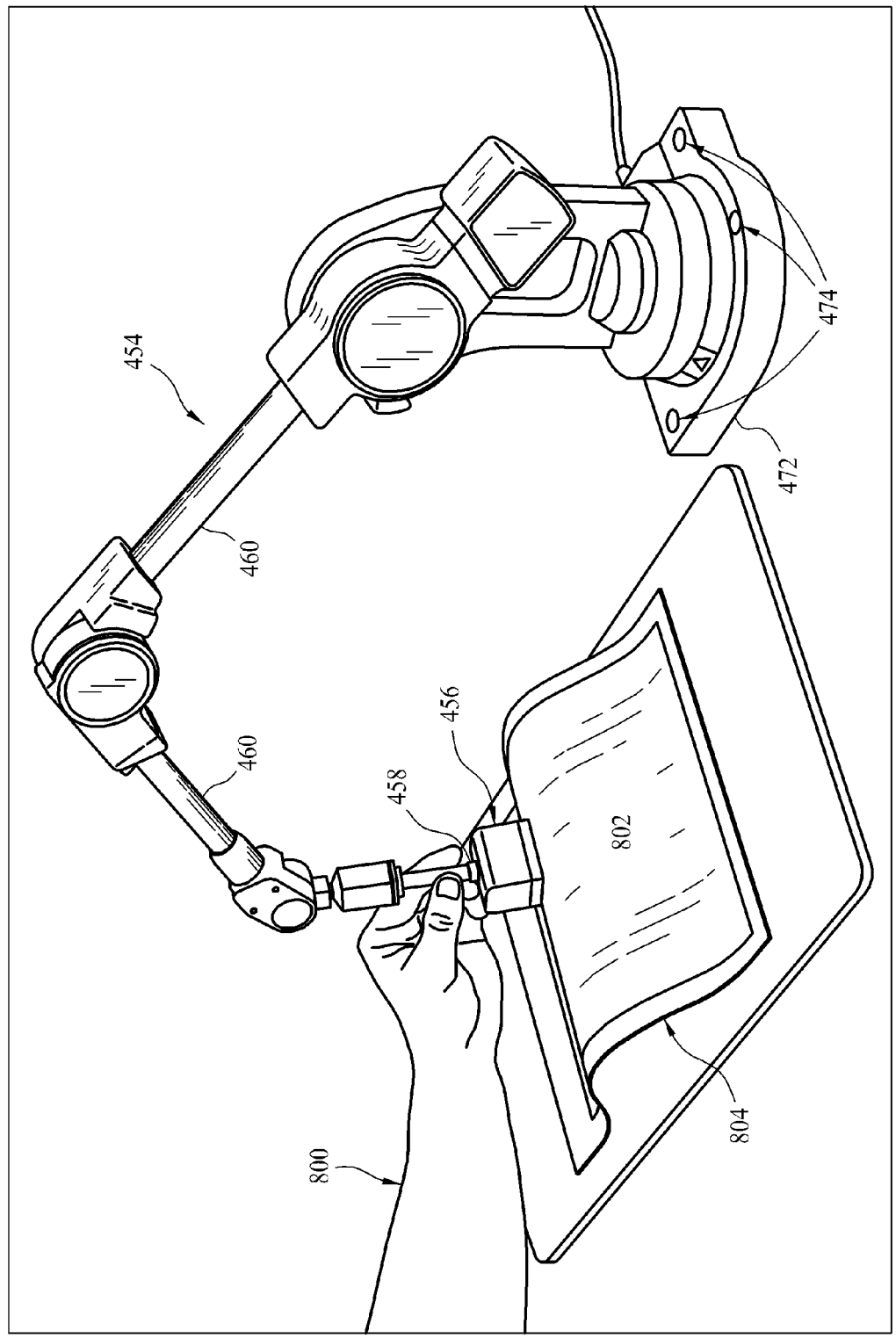
FIG. 8A is a depiction of a user operating the six degree-of-freedom digitizer of FIGS. 4, 5, and 6.

In some embodiments, digitizer 454 is vacuum-mounted (such as with vacuum cups 470 attached to its base 472) which allows for temporary attachment onto a structure (such as wing 402) being inspected or repaired. In other embodiments, digitizer is mounted on a device such that it is proximate to the structure being inspected or repaired. A position and an orientation of digitizer 454 are determined relative to an aircraft coordinate system using LPS 452. Mounted to the distal end 458 of the digitizer 454 is sensor 456 (as shown in FIG. 8A), which in one embodiment, is a linear ultrasonic array sensor. Digitizer 454 operates to provide a position of distal end 458, and therefore of sensor 456. The positions of reference points 474 on digitizer 454, for example, at the base 472 of digitizer 454, are in a known pattern relative to the digitizer coordinate system, and by using this information along with the position measurements collected by the LPS 452 for these same points, the position and orientation of the base 472 can be determined in aircraft coordinates, including for such embodiments where the base 472 is not attached directly to the aircraft. A position and orientation of the sensor 458, in six-dimensional space relative to the aircraft, can therefore be precisely calculated, in aircraft coordinates, throughout its range of movement.

It should be noted that other sensors other than a linear ultrasonic array sensor can be attached to distal end 458 of digitizer 454, depending upon the application. In the embodiment illustrated by FIG. 4, sensor 456 is an ultrasonic array. Other sensors include a linear ultrasonic sensor array, an ultrasonic resonance sensor array, an eddy current sensor array, a magneto-resistive sensor array, a magnetic sensor array, and a linear infrared array to name a few. In some embodiments, a second or even a third sensor array can be positioned next to the initial sensor so that more than one NDE modality can be collected, for better discrimination and analysis of structural flaws, variations, and/or damage.

Figure 6:
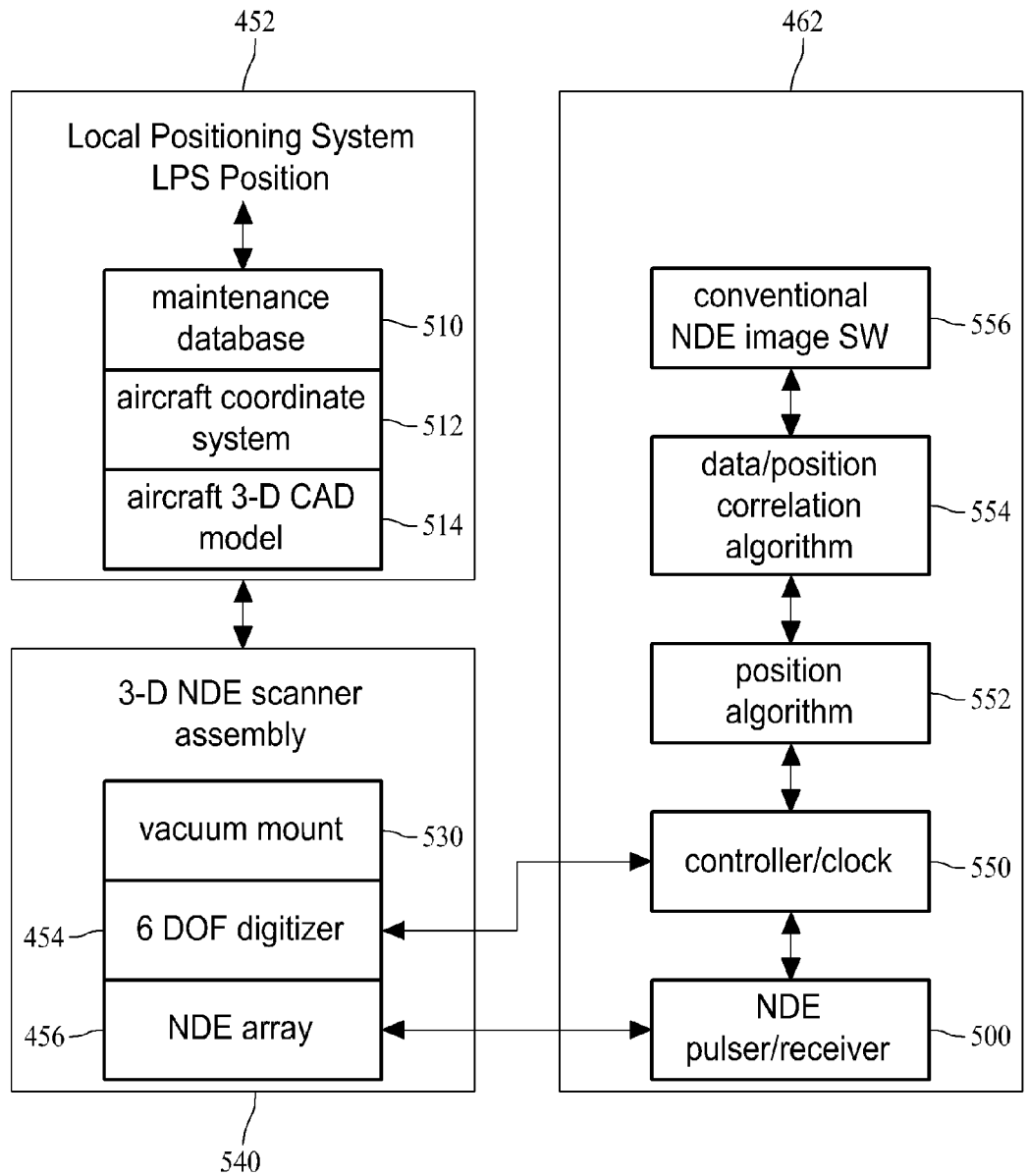
FIG. 6 is a block diagram of an inspection system including a local positioning system, a non-destructive evaluation scanner assembly and a processing device.

FIG. 6 is a block diagram of inspection system 450. As shown, sensor array 456 is communicatively coupled to an NDE data sender/receiver 500 within processing device 462. One embodiment of an NDE data sender/receiver 500 is an ultrasonic pulser/receiver with a data collection, storage, and digital display capability provided internally, or with a separate tablet or laptop computer (not shown). In some embodiments, NDE data sender/receiver 500 is a multichannel sender/receiver and is used to interrogate the structure (wing 402) at each sensor, allowing the rapid collection of data.

The position and orientation of each sensor element (and therefore, the array) is automatically computed and correlated with the data collected at that position and orientation. Data is collected at each sensor element of sensor array 456 at a particular time and correlated with its position, as determined by the position and orientation of the distal end 458 of the digitizer 454. The collected NDE data is transferred into the aircraft coordinate system, and the resulting three-dimensional model, including knowledge of the specific location and underlying/adjacent structure is used to validate and/or improve damage and repair assessments, for example, zoned porosity measurements. The communication connection between the scanner assembly (digitizer 454 and sensor 456) and processing device 462 may be wired or wireless.

As shown in FIG. 6, LPS 452 includes data relating to a maintenance database 510, related to the structure, data 512 indicative of the structure coordinate system, and a three-dimensional CAD model 514 of the structure. In combination, digitizer 454, sensor 456 and vacuum mount system 530 may be referred to as a three-dimensional non-destructive evaluation (NDE) scanner assembly 540. Processing device 462 includes the NDE sender/receiver 500 as described herein, and further includes, for example, a controller/clock 550, a positioning algorithm 552, a NDE data/position correlation algorithm 554, and a conventional NDE imaging program 556.

Figure 7:
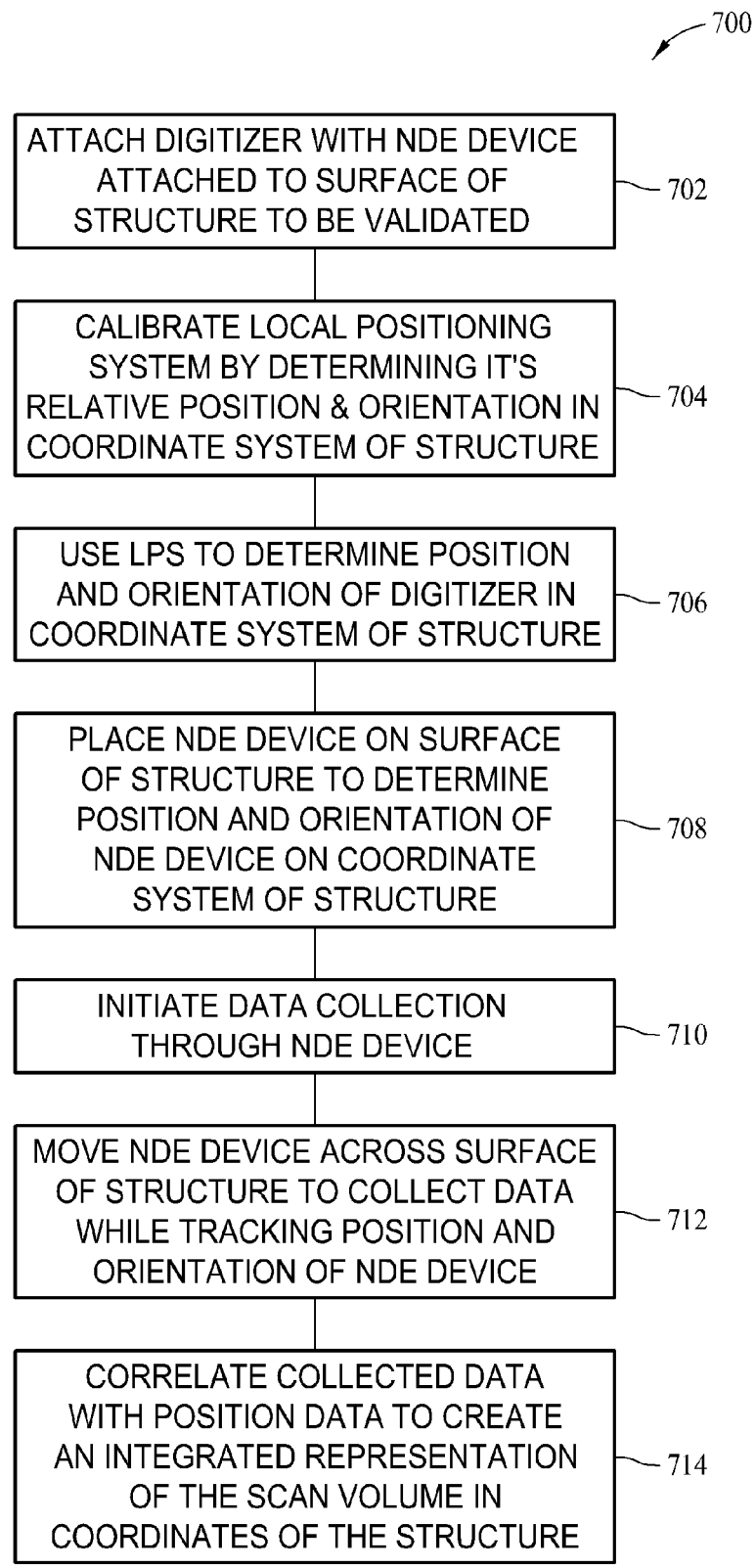
FIG. 7 is a flowchart that illustrates the process for validation of a composite structure such as a structure that has undergone a repair operation.

FIG. 7 is a flowchart 700 that further illustrates the process for validation of a composite structure, for example, a structure that has undergone a repair operation. More specifically, flowchart 700 describes determining a position and an orientation of a six degree-of-freedom (DOF) digitizer with respect to structure coordinates and using a NDE sensor with the digitizer to provide NDE test results expressed in aircraft coordinates. As described elsewhere herein, the embodiments provide a portable, low cost system for composite repair validation and NDE on highly complex contoured composite structures.

Referring specifically to the flowchart 700, the six-DOF digitizer 454 is attached 702 to the surface of the structure to be tested and/or otherwise evaluated. In some embodiments, the NDE sensor array 456 is attached either before or after the digitizer 454 is attached to the structure. More specifically, an ultrasonic or other sensor array is attached to the distal end 458 of the six-DOF digitizer 454 for increased scan coverage speed (since an array of sensors reduces the number of required scan steps). As described herein, in some embodiments, the digitizer 454 is attached adjacent to the area to be inspected using vacuum mounts 470 attached to its base 472.

In other embodiments, the six-DOF digitizer 454 is attached to a fixture or other tooling in the vicinity of the target structure (wing 402). In these situations the six-DOF digitizer 454 remains stationary after calibration with the structure, or has access to data describing any change in the relative position and orientation relative to the structure. In some embodiments the six-DOF digitizer 454 is attached to its support using vacuum mounts 470 or other types of attachments.

The local positioning system (LPS) 452 is calibrated 704 by determining the relative position and orientation of the LPS 452 in the coordinate system of the structure. Specifically, the LPS 452 measures the position of three reference points 474 of known position on the structure to determine the relative position of the LPS device 452 to the coordinate system of the structure. The LPS 452 then determines 706 the position and orientation of the six-DOF digitizer 454 in the coordinate system of the structure by using the LPS measured positions of three reference points 474 on the six-DOF digitizer 454 (usually on the base 472), allowing the relative coordinates of data taken by the array at the distal end of the digitizer to be transformed into absolute coordinates of the structure.

An operator prepares the NDE pulser-receiver 500 and remainder of processing device 462 to collect data from the NDE sensor array 456. The operator moves 708 the distal end 458 of the digitizer 454, along with the attached NDE sensor array 456, placing it on the surface of the repair or other structure and operates the processing device to determine and otherwise define the position and orientation of the NDE sensor array 456 in the coordinate system of the structure and initiates 710 the data collection process associated with the NDE sensor array 456.

The operator moves 712 the NDE array (sensor 456), attached to the distal end 458 of the digitizer 454, over the surface area, for example, of the repair, covering the area to be inspected. Six degrees-of-freedom (DOF) are required to fully define the position and orientation of the distal end 458 of the digitizer 454 and therefore the NDE sensor array 456. The six-DOF digitizer 454 allows relatively free hand scanning by the user, for example, a natural human motion, essentially "painting" the area to be inspected with the NDE sensor array 456. The sequence of positions representing this motion can be displayed on a PC monitor (not shown) to help guide the operator during the free-hand scanning process. This type of real-time display helps the operator to make sure the area of interest has been fully covered.

During the movement 712 of the NDE sensor array 456 across the surface, inspection data is collected and the position and orientation, again in coordinates of the structure, are tracked. More specifically, each of the individual scan samples collected by the NDE sensor array 456 is correlated 714 with the corresponding 6-DOF position and orientation data sample for the distal end 458 to create an integrated representation of the scan volume defined in the coordinate system of the structure.

Once the data is collected, it can be analyzed using the signal return amplitude and time-of-flight, as well as sensor position and orientation data. Ultrasonic attenuation at material thicknesses in zones of a repair can be measured to quantify porosity, if it exists. Defects such as delamination, disbonds, and foreign material in a repair or other structure can be quantified as well. Since the scanning operation described above is in absolute structural coordinates, the underlying CAD structure (CAD model 514) and maintenance database 510 can be referenced for improved assessment and information about previous repairs.

If the surface area of the structure to be inspected is larger than the reach of the articulating arm 460 of six-DOF digitizer 454, or another area requires inspection, digitizer 454 may be moved to another area of the structure, and the above described process reinitiated where the LPS 452 is utilized to determine 706 a new position and orientation of the digitizer 454.

Figure 8B:
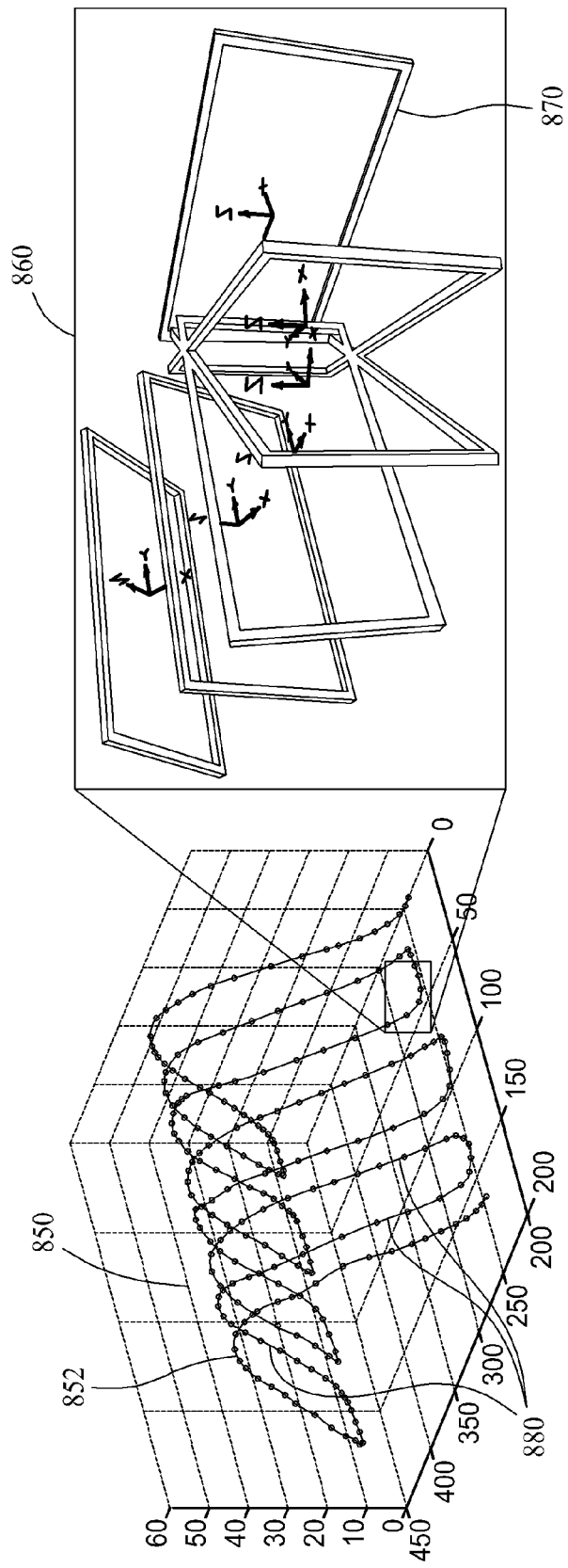
FIG. 8B illustrates position tracking data collected for the curved surface of FIG. 8A as well as position and orientation data aligned with scan slice frames.

The NDE data, such as the ultrasound amplitude or time-of-flight, scan can be shown and analyzed in three-dimensional space. FIGS. 8A and 8B provide an illustration of the distal end 458, and therefore the sensor 456 of digitizer 454 being moved over a curved surface and the resulting digitizer tracking data.

More specifically, FIG. 8A is a depiction of an operator 800 operating the six-DOF digitizer 454 of FIGS. 4, 5, and 6 including an NDE sensor array (sensor 456) mounted at the distal end 458 of articulating arm 460 thereof across the surface 802 of a highly contoured object 804. FIG. 8B shows a three dimensional plot 850 of the position tracking data 852 collected for the object 804 as the operator 800 moved the sensor 456 over the curved surface 802.

The six-DOF digitizer 454 also collects orientation data during the scan, a subset of which is shown in scan slice frames 860. Scan slice frames 860 represent the scan data provided by the sensor 456. Together the position tracking data 852 and orientation data are used to register the corresponding scans for each frame 870 to properly align the frames 870 in coordinates of the structure. FIG. 8B includes position tracking data 852 collected for curved surface 802 as well as position and orientation data aligned with scan slice frames 860. The sample points 880 in the plot of FIG. 8B represent some of the position and orientation samples that are used to generate 4×4 transformation matrices for the alignment process. Each transformation matrix is applied to the corresponding scan slice frame 870 (captured concurrently with the digitizer arm tracking data) to properly align the scans with the coordinate system of the structure.

The described embodiments are faster than the portable UT handheld systems described above, and provide a representation of the interior of the structure required for many types of inspections. The described embodiments are a portable, low cost system for composite repair validation and NDE on highly complex contoured composite structures.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-destructive evaluation system for a structure comprising:
   a local positioning system (LPS) configured for determining position and orientation of objects relative to a coordinate system of the structure;
   a six degree-of-freedom digitizer operable for at least one of temporary attachment to the structure and placement proximate the structure, said digitizer comprising a base and an articulated arm extending from said base and having a distal end, said local positioning system further configured for determining a position of said base of said digitizer in the coordinate system of the structure, said digitizer configured to determine a position and an orientation of said distal end of the digitizer with respect to said base;
   a non-destructive evaluation sensor array configured for attachment to said distal end of said articulated arm for movement across a surface of the structure in multiple positions and orientations;
   a processing device configured to determine position and orientation data for said non-destructive evaluation sensor array based on the position and orientation of said digitizer base as calculated by said local positioning system and the position and orientation of said distal end of said digitizer as provided by said digitizer, said processing device further configured to operate said sensor array for collection of scan samples relating to the structure and correlate the individual scan samples with the corresponding position and orientation data relating to said distal end of said digitizer to create an integrated representation of the scan volume of the structure, defined in the coordinate system of the structure; and
   wherein said digitizer base includes reference points thereon, wherein the reference points are in a known pattern relative to a digitizer coordinate system such that by using the reference points along with position measurements collected by the LPS for the reference points, the position and orientation of the base can be determined.

2. The non-destructive evaluation system according to claim 1 wherein said non-destructive sensor array comprises at least one of a linear ultrasonic sensor array, an ultrasonic resonance sensor array, an eddy current sensor array, a magneto-resistive sensor array, a magnetic sensor array, and a linear infrared array.

3. The non-destructive evaluation system according to claim 1 wherein said non-destructive sensor array comprises a plurality of sensor arrays so that data relating to more than one non-destructive evaluation modality can be collected by said processing device.

4. The non-destructive evaluation system according to claim 1 wherein said base of said digitizer is operable for temporary attachment onto the structure being inspected.

5. The non-destructive evaluation system according to claim 1 wherein said processing device comprises a non-destructive evaluation data sender/receiver communicatively coupled to said non-destructive sensor array.

6. The non-destructive evaluation system according to claim 5 wherein said non-destructive evaluation data sender/receiver comprises a multiple channel sender/receiver.

7. The non-destructive evaluation system according to claim 1 wherein said processing device is configured to correlate data collected from said non-destructive sensor array with a time of the data collection and the position and orientation of said non-destructive sensor array.

8. The non-destructive evaluation system according to claim 7 wherein said processing device is configured to generate a three-dimensional model of the structure, in the coordinate system of the structure, using the correlated data from said non-destructive sensor array, with the model used for validation.

9. The non-destructive evaluation system according to claim 8 wherein said LPS comprises at least one of data relating to a maintenance database for the structure and a three-dimensional CAD model of the structure for comparison with the generated three-dimensional model of the structure.

10. A method for validating the integrity of a composite structure, said method comprising:
  locating a six degree-of-freedom digitizer proximate a surface of the structure proximate an area to be validated;
  determining a position and an orientation of a reference portion of the digitizer in a coordinate system of the structure, wherein the reference portion of the digitizer is located on a base of the digitizer, and wherein the reference portion includes reference points in a known pattern relative to a digitizer coordinate system such that by using the reference points along with position measurements collected for the reference points, a position and orientation of the base can be determined;
  configuring a distal end of an articulating arm of the six degree-of-freedom digitizer with a non-destructive evaluation sensor array;
  moving the non-destructive evaluation sensor array across the surface of the structure to be validated;
  tracking a position and orientation for the non-destructive evaluation sensor array based on the determined position and orientation of the reference portion of the digitizer and the position and orientation of the distal end of the digitizer with respect to the determined position and orientation of the reference portion of the digitizer;
  correlating data from the non-destructive evaluation sensor array with the position and orientation data from the distal end of the digitizer; and
  generating an integrated representation of the scan volume of the structure, defined in the coordinate system of the structure.

11. The method according to claim 10 wherein determining a position and an orientation of the digitizer in the coordinate system of the structure comprises determining a position and an orientation of a base of the digitizer base in the coordinate system of the structure using a local positioning system.

12. The method according to claim 11 wherein tracking a position and orientation for the non-destructive evaluation sensor array comprises transforming the coordinates associated with the data collected by the non-destructive evaluation sensor array at the distal end of the digitizer into absolute coordinates of the structure based on the position of the digitizer base.

13. The method according to claim 10 wherein moving the non-destructive evaluation sensor array across the surface of the structure to be validated comprises using six degrees-of-freedom movement of the distal end of the digitizer to allow relatively free hand scanning of the surface with the non-destructive evaluation sensor array.

14. The method according to claim 10 wherein generating an integrated representation of the scan volume of the structure comprises comparing a three-dimensional model of the structure, generated from non-destructive sensor array data, to at least one of data relating to a maintenance database for the structure and a three-dimensional CAD model of the structure.

15. The method according to claim 10 wherein configuring a distal end of an articulating arm of the six degree-of-freedom digitizer comprises attaching at least one of a linear ultrasonic sensor array, an ultrasonic resonance sensor array, an eddy current sensor array, a magneto-resistive sensor array, a magnetic sensor array, and a linear infrared array to the distal end of the articulating arm.

16. The method according to claim 10 wherein generating an integrated representation of the scan volume of the structure comprises using correlated position and orientation data to register scans for each frame of non-destructive evaluation sensor array data to properly align the frames in the coordinates of the structure.

17. A non-destructive inspection system for a structure comprising:
  a six degree-of-freedom digitizer comprising a base and an articulated arm extending from said base and having a distal end, said digitizer configured to determine a position and an orientation of said distal end with respect to said base;
  a local positioning system operable for determining a position and an orientation of said digitizer base in a coordinate system of the structure;
  a non-destructive evaluation sensor array attached to said distal end of said digitizer;
  a processing device configured to operate said sensor array for collection of scan samples relating to the structure from said sensor array as said sensor array is moved across said structure, said processing device further configured to correlate the individual scan samples from said sensor array with corresponding position and orientation data relating to said sensor array from said digitizer and the position and orientation of said digitizer base from said local positioning system; and
  wherein said digitizer base includes reference points thereon, wherein the reference points are in a known pattern relative to a digitizer coordinate system such that by using the reference points along with position measurements collected for the reference points, the position and orientation of the base can be determined.

18. The non-destructive inspection system for a structure according to claim 17 wherein said processing device is configured to generate an integrated representation of the scan volume of the structure using correlated position and orientation data to register scans for each frame of non-destructive evaluation sensor array data to properly align the frames in the coordinates of the structure.

19. The non-destructive inspection system for a structure according to claim 17 wherein said processing device is configured to compare a three-dimensional model of the structure, generated from non-destructive sensor array data, to at least one of data relating to a maintenance database for the structure and a three-dimensional CAD model of the structure.

* * * * *